(12) United States Patent
Vahala (10) Patent No.: US 9,977,104 B2
(45) Date of Patent: May 22, 2018

(54) MAGNETIC RESONANCE IMAGING ALONG ENERGY-DELIVERING DEVICE AXIS

(71) Applicant: KONINKLIJKE PHILIPS N.V., Eindhoven (NL)

(72) Inventor: Erkki Tapani Vahala, Hyvinkaa (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 414 days.

(21) Appl. No.: 14/405,316

(22) PCT Filed: Jun. 3, 2013

(86) PCT No.: PCT/IB2013/054581
§ 371 (c)(1),
(2) Date: Dec. 3, 2014

(87) PCT Pub. No.: WO2013/182977
PCT Pub. Date: Dec. 12, 2013

(65) Prior Publication Data
US 2015/0148659 A1 May 28, 2015

Related U.S. Application Data (60) Provisional application No. 61/655,015, filed on Jun. 4, 2012.

(51) Int. Cl.
*G01R 33/48* (2006.01)
*G01R 33/385* (2006.01)
(Continued)

(52) U.S. Cl.
CPC ........ *G01R 33/4808* (2013.01); *A61B 5/0037* (2013.01); *A61B 5/015* (2013.01); *A61N 7/02* (2013.01); *A61N 7/022* (2013.01); *G01R 33/30* (2013.01); *G01R 33/3856* (2013.01); *G01R 33/4804* (2013.01); *G01R 33/4814* (2013.01); *G01R 33/543* (2013.01);
(Continued)

(58) Field of Classification Search
CPC .... A61B 2018/00791; A61B 2090/374; A61B 5/0037; A61B 5/015; A61B 5/4836; A61N 7/02; A61N 7/022; G01R 33/30; G01R 33/3856; G01R 33/4804; G01R 33/4808; G01R 33/4814; G01R 33/543
See application file for complete search history.

(56) References Cited

U.S. PATENT DOCUMENTS 8,000,445 B2 8/2011 Mollus
8,229,544 B2 7/2012 Tseng et al.
(Continued)

OTHER PUBLICATIONS

Hynynen, K. et al "MRI Guided and Monitored Focused Ultrasound Thermal Ablation Methods: A Review of Progress", International Journal of Hyperthermia, vol. 20, No. 7, Nov. 2004, pp. 725-737.

*Primary Examiner* — Michael Rozanski (57) ABSTRACT

Location data indicative of the location of a target volume (146) is received. A positioning system (224) rotates a therapy device including an energy-delivering device about a longitudinal axis. The energy-delivering device delivers energy to the target volume (146) at a first rotation position using the location data: A magnetic resonance imaging scanner (106) acquires first magnetic resonance data from a first set of slice planes (509) and a second set of slice planes (501, 505, 507) of the target volume (146) at least one second rotation position of the therapy device.

16 Claims, 5 Drawing Sheets

(51) Int. Cl.

| | |
|---|---|
| *A61N 7/02* | (2006.01) |
| *A61B 5/00* | (2006.01) |
| *A61B 5/01* | (2006.01) |
| *G01R 33/54* | (2006.01) |
| *G01R 33/30* | (2006.01) |
| A61B 18/00 | (2006.01) |
| A61B 90/00 | (2016.01) |

(52) U.S. Cl.
CPC ... *A61B 5/4836* (2013.01); *A61B 2018/00791* (2013.01); *A61B 2090/374* (2016.02)

(56) References Cited

U.S. PATENT DOCUMENTS

| | | |
|---|---|---|
| 2007/0239062 A1 | 10/2007 | Chopra |
| 2009/0196480 A1 | 8/2009 | Nields et al. |
| 2010/0014740 A1 | 1/2010 | Movassaghi |
| 2011/0135186 A1 | 6/2011 | Bakker |
| 2011/0137147 A1 | 6/2011 | Skliar et al. |
| 2012/0053448 A1 | 3/2012 | Griswold |
| 2012/0070058 A1 | 3/2012 | Raju |

MAGNETIC RESONANCE IMAGING ALONG ENERGY-DELIVERING DEVICE AXIS

TECHNICAL FIELD

The invention relates to energy treating devices, in particular to the use of ultrasound transducers for high intensity focused ultrasound.

BACKGROUND OF THE INVENTION

With recent advances in medical imaging and ultrasound technology, interest in high-intensity focused ultrasound (HIFU) ablation of tumors has increased. Tumor ablation is performed by heating volumes within the tumor until an accumulated thermal dose is reached. Therefore, reliable real-time temperature monitoring with Magnetic Resonance Imaging (MRI) scanner is necessary to ensure a sufficient thermal necrosis to the target while avoiding excessive heating and damage of surrounding healthy tissues.

US 2012/0053448 A1 discloses a method to adjust the scan plane in dependence on the shape of an interventional instrument.

SUMMARY OF THE INVENTION

Embodiments of the invention may provide for a medical apparatus, a computer program product and a method for controlling a medical apparatus in the independent claims. Embodiments are given in the dependent claims.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic resonance image data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for cumulated temperature between treatments heating outside treatment area.

Other imaging methods may also be used if the energy deposition does not measurably affect the temperature of the energy deposition volume. For example, tissue necrosis from radiation damage or targeted drug release may show up in perfusion or diffusion MR images. Also, the oxygen concentration can be measured to assess the efficiency and to provide therapy feedback.

The term "thermal dose" as used herein refers to the accumulated damage to tissue cells induced by heating.

The term "transducer element" refers to a single emitting ultrasound element in a transducer comprising of many independently controllable elements.

In one aspect, the invention relates to a medical apparatus comprising a magnetic resonance imaging module for acquiring magnetic resonance data from nuclei of a subject located within an imaging volume; a therapy device comprising an energy-delivering device for delivering energy to a target volume within the imaging volume, the therapy device being operable to rotate about a longitudinal axis of the therapy device; a positioning system for rotating the therapy device; a memory for storing machine executable instructions; and a processor for controlling the medical apparatus.

Execution of the machine executable instructions causes the processor to receive location data indicative of the location of the target volume. The location of the target volume may represent coordinates of the target volume with respect to an MRI module reference frame. Execution of the machine executable instructions further causes the processor to control the positioning system to rotate the therapy device about the longitudinal axis. The rotation may be automatic or manual. This may have the advantage of positioning precisely the catheter on a rotation trajectory about the longitudinal axis. Execution of the machine executable instructions further causes the processor to control the energy-delivering device to deliver energy to the target volume at a first rotation position relative to the longitudinal axis on a rotation trajectory of the therapy device using the location data. Execution of the machine executable instructions further causes the processor to determine a first set of slice planes of the target volume at the first rotation position to be imaged by the magnetic resonance imaging module. Execution of the machine executable instructions further causes the processor to control the magnetic resonance imaging module to acquire first magnetic resonance data from the first set of slice planes. A reconstructed image from the first magnetic resonance data from a particular slice is typically represented as a two-dimensional graph or field. Execution of the machine executable instructions further causes the processor to determine a second set of slice planes of the target volume at at least one second rotation position on the rotation trajectory to be imaged by the magnetic resonance imaging module; and control the magnetic resonance imaging module to acquire second magnetic resonance data from the second set of slice planes.

Said features provide in addition to the data acquired from fixed slice planes (at a fixed position of the therapy device) data from rotating slice planes positioned at different rotation positions on the rotation trajectory of the therapy device. That is, the acquired data covers a large 3D volume. This is advantageous in that this method is less time consuming compared to the conventional methods. In fact, to cover a large 3D volume in the region of interest, these conventional fixed slice plane methods require an extended field of view of the slice planes in order to acquire data outside the transducer elements which takes long time and slows down the acquisition system. The fixed slice plane methods also necessitate more slices and small slice thickness to provide equal resolution along the longitudinal axis.

According to one embodiment, the therapy device comprises a catheter, wherein the energy-delivering device comprises an ultrasound transducer, wherein the ultrasound transducer is a linear phased array being mounted into a distal end of the catheter, wherein delivering energy to the target volume comprises heating the target volume, wherein the first magnetic resonance data comprises first magnetic thermometry resonance data, wherein the second magnetic resonance data comprises second magnetic thermometry resonance data. The heating of the target volume may be done for example by driving (or adjusting) transducer elements of the ultrasound transducer to selectively focus a beam of ultrasonic energy from the ultrasound transducer into the target volume. This may also be done for example by driving (or adjusting) transducer elements of the ultrasound transducer to selectively turn on a non-focused beam of ultrasonic energy from the ultrasound transducer into the target volume.

This is advantageous in that the temperature mapping in the target volume is accurate due to the improved resolution, which ensures that the thermal dose is properly reached.

The therapy device may comprise a laser induced thermotherapy device.

The therapy device may also comprise a microwave and/or radiofrequency induced thermotherapy device.

The therapy device may also comprise an external, rotating linear accelerator gantry.

According to one embodiment, the medical apparatus further comprises a gradient coil, a radio-frequency coil and a coil control devices, wherein the control of the magnetic resonance imaging module to acquire second magnetic resonance data comprises controlling the coil control devices to derive the gradient coil to generate a respective first magnetic gradient field and to derive the radiofrequency coil to generate a respective first radio-frequency field for each of the second set of slice planes in accordance with the second rotation position.

According to one embodiment, the control of the magnetic resonance imaging module to acquire first magnetic resonance data comprises controlling the coil control devices to derive the gradient coil to generate a respective second magnetic gradient field and to derive the radiofrequency coil to generate a respective second radio-frequency field for each of the first set of slice plans in accordance with the first rotation position.

The gradient coils are used to produce variations in the main magnetic field ($B_0$) of the magnetic resonance imaging module as well as radiofrequency (RF) coils are used to produce radio frequency pulse modification in order to localize and produce a slice plane in accordance with the first and/or second rotation position. This may be advantageous as it provides an accurate positioning of the slice plane and generates radio frequency excitation that only points desired spins into the slice plane.

According to one embodiment, the execution of the machine executable instructions further causes the processor to control the coil control devices to derive the gradient and RF coils to dynamically change the field-of-view in addition to the position of the first and second slice planes during the therapy. This may be advantageous as it can be used to zoom in to a critical structure for more accurate dose determination, or to check unwanted heating outside the normal field-of-view.

According to one embodiment, execution of the machine executable instructions further causes the processor to acquire the second magnetic resonance thermometry data and second magnetic resonance morphological data from the second set of slice planes with an interleaved pulse sequence.

According to one embodiment, execution of the machine executable instructions further causes the processor to acquire the first magnetic resonance thermometry data and first magnetic resonance morphological data from the first set of slice planes with an interleaved pulse sequence.

The morphological data may be diagnostic image data of clinically high quality for visualizing the target volume. The magnetic resonance thermometry data may be produced with high temporal resolution compared to the magnetic resonance morphological data, or magnetic resonance thermometry data may be produced with different techniques that have different time requirements. A reconstructed image from the magnetic resonance thermometry data may be superimposed on a reconstructed image from magnetic resonance morphological data. This is beneficial in that interleaved data provide high spatial resolution data to accurately measure the temperature distribution and high temporal resolution data to track changes (e.g. increase) in the temperature.

According to one embodiment, execution of the machine executable instructions further causes the processor to concurrently acquire the first and second magnetic resonance data. That is, the data are acquired on short time period and cover a large 3D volume. For example, the heating may induce fast temperature change in the target volume and acquiring thermometry data on short time is required in order to properly control the energy deposition.

According to one embodiment, each of the first and second set of slice planes comprises one slice plane oriented in parallel to the longitudinal axis.

According to one embodiment, each of the first and second set of slice plans further comprises one or more parallel slice planes parallel to the longitudinal axis.

According to one embodiment, each of the first and second set of slice plans further comprises one or more fan-shaped slice planes parallel to the longitudinal axis.

According to one embodiment, each of the first and second set of slice planes further comprises planes being arranged along the longitudinal axis.

The first set of slice planes may be determined at a non-rotating position. That is, the first set of slice planes is a fixed set of slice planes. These first slice planes further comprise transaxial planes perpendicular to the longitudinal axis. The second set of slice planes is rotated in relation to the catheter rotation following the rotation trajectory. The rotation may be piece-wise jumps to fixed angles on the rotation trajectory with respect to the longitudinal axis and/or lag or lead the catheter rotation with a known relation. This allows visualizing clinically useful heating effects before and after the actual active heating. Such effects can be perfusion, diffusion, and heat transfer within the tissues.

According to one embodiment, execution of the machine executable instructions further causes the processor to receive a treatment plan comprising instructions for controlling the operation of the ultrasound transducer; acquire one or more reference images of the target volume at predetermined positions relative to the longitudinal axis in a rotation trajectory of the catheter; calculate a temperature change between the first and second set of slice planes and the respective one or more reference images; and control the operation of the ultrasound transducer to correct for the temperature change.

The temperature change measurement provides a clinician with accurate temperature measurement and real-time thermometry data. Thus, the temperature may be optimized and adjusted continuously by using for example a proportional, integral and derivative (PID) controller. The PID controller may update the power level of the catheter according to the temperature change taking into account the physical characteristics such as perfusion, diffusion and absorption of the target volume. The PID controller may also adjust the rotation speed of the catheter. This ensures a well-controlled border between preserved and destroyed tissue created during the heating of the target volume.

According to one embodiment, the ultrasound transducer comprises multiple ultrasound transducer elements, wherein execution of the machine executable instructions further causes the processor to receive a first thermal map of the target volume; receive a treatment plan comprising instructions for controlling the operation of the ultrasound transducer using the first thermal map; determine a second thermal map by using the first and second magnetic resonance thermometry data; and control the multiple ultrasound transducer elements to adjust heating the target volume in accordance with the first and second thermal maps.

According to one embodiment, the adjustment of the multiple ultrasound transducer elements comprises supplying the transducer elements with electrical excitations having adjustable phases in order to apply appropriate phase to each transducer element.

According to one embodiment, the execution of the machine executable instructions further causes the processor to adjust a field-of-view and position of the first and second set of slice plans. This allows for covering an area outside the transducer elements and thus covering a large 3D volume.

In another aspect, the invention relates to a computer program product containing machine executable instructions for execution by a processor controlling a medical apparatus, wherein the medical apparatus comprises a magnetic resonance imaging module for acquiring magnetic resonance data from nuclei of a subject located within an imaging volume; a therapy device comprising an energy-delivering device for delivering energy to a target volume within the imaging volume, the therapy device being operable to rotate about a longitudinal axis of the therapy device; a positioning system for rotating the therapy device; wherein execution of the machine executable instructions causes the processor to:
  receive location data indicative of the location of the target volume;
  control the positioning system to rotate the therapy device about the longitudinal axis;
  control the energy-delivering device to deliver energy to the target volume at a first rotation position relative to the longitudinal axis on a rotation trajectory of the therapy device using the location data;
  determine a first set of slice planes of the target volume at the first rotation position to be imaged by the magnetic resonance imaging module;
  control the magnetic resonance imaging module to acquire first magnetic resonance data from the first set of slice planes;
  determine a second set of slice planes of the target volume at at least one second rotation position on the rotation trajectory to be imaged by the magnetic resonance imaging module; and
  control the magnetic resonance imaging module to acquire second magnetic resonance data from the second set of slice planes.

In another aspect, the invention relates to a method of controlling a medical apparatus, wherein the medical apparatus comprises a magnetic resonance imaging module for acquiring magnetic resonance thermometry data from nuclei of a subject located within an imaging volume; a therapy device comprising an energy-delivering device for delivering energy to a target volume within the imaging volume, the therapy device being operable to rotate about a longitudinal axis of the therapy device; a positioning system for rotating the therapy device; the method comprising:
  receiving location data indicative of the location of the target volume;
  controlling the positioning system to rotate the therapy device about the longitudinal axis;
  controlling the energy-delivering device to deliver energy the target volume at a first rotation position relative to the longitudinal axis on a rotation trajectory of the therapy device using the location data;
  determining a first set of slice planes of the target volume at the first rotation position to be imaged by the magnetic resonance imaging module;
  controlling the magnetic resonance imaging module to acquire first magnetic resonance data from the first set of slice planes;
  determining a second set of slice planes of the target volume at at least one second rotation position on the rotation trajectory to be imaged by the magnetic resonance imaging module; and
  controlling the magnetic resonance imaging module to acquire second magnetic resonance data from the second set of slice planes.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function.

Elements which have been discussed previously will not necessarily be discussed in later figures if the function is equivalent.

Figure 1:
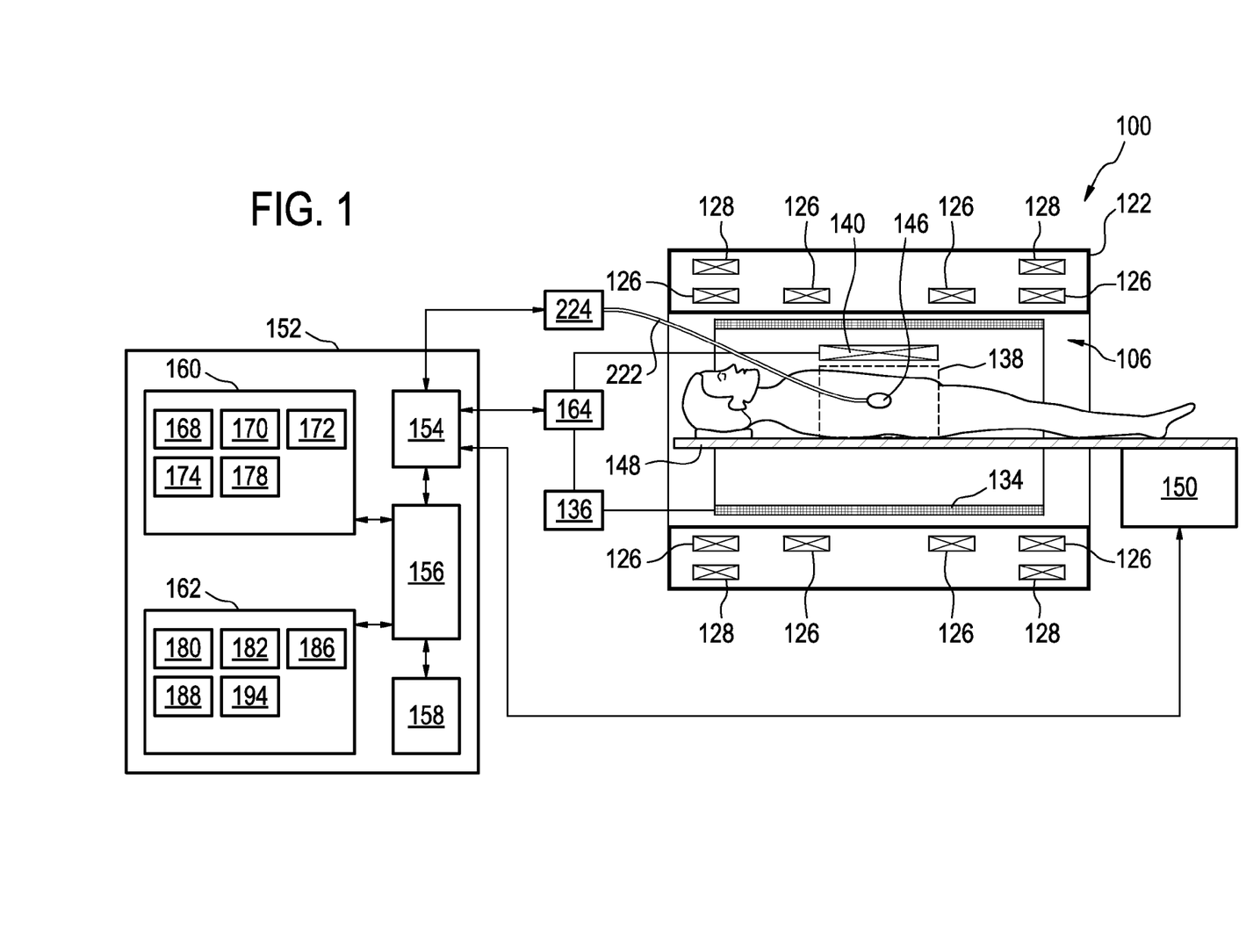
FIG. 1 shows a cross-sectional and functional view of a medical apparatus.

FIG. 1 shows a cross-sectional and functional view of a medical apparatus 100. The medical apparatus 100 is shown as comprising a magnetic resonance imaging module 106. The magnetic resonance imaging module 106 is shown as comprising a magnet 122. The magnet 122 shown in FIG. 1 is a cylindrical type superconducting magnet. However, other magnets are also applicable for embodiments of the invention. The magnet 122 has a supercooled cryostat 124. Inside the cryostat 124 there is a collection of superconducting coils 126. There are also compensation coils 128 whose current opposes the direction of current in the superconducting coils 126.

Within the bore of the magnet there is a magnetic field gradient coil 134 which is used for acquisition of motion tracking magnetic resonance data and image magnetic resonance data to spatially encode objects within an imaging volume 138 of the magnet 122. The magnetic field gradient coil 134 is connected to a magnetic field gradient coil power supply 136 and a coil control devices 164. The magnetic field gradient coil 134 is intended to be representative. Typically magnetic field gradient coils contain three separate sets of coils for spatially encoding in three orthogonal spatial directions. The imaging volume 138 is located in the center of the magnet 122.

Adjacent to the imaging volume 138 is a radio frequency coil 140 for manipulating the orientations of magnetic spins within the imaging volume 138 and for receiving radio transmissions from spins also within the imaging volume 138. The radio frequency coil 140 is connected to the coil control devices 164. It is understood that the radio frequency coil 140 is simply representative.

Within the center of the magnet is also located a subject 144. The subject 144 has a target volume 146 and is shown as reposing on a subject support 148. The subject support 148 has a mechanical positioning system 150 (optional). The mechanical positioning system 150 is adapted for positioning the subject 144 within the magnet 122. Depending upon the space available inside of the magnet the subject support 148 may be adapted for moving the subject in different directions. The coil control devices 164 and the mechanical positioning system 150 are all shown as being connected to a hardware interface 154 of a computer system 152. The computer system 152 uses a processor 156 to control the medical apparatus 100.

A catheter 222 has been inserted into the subject 144. The distal end of the catheter 222 is within the imaging volume 138. The catheter 222 comprises an ultrasound transducer. The ultrasound transducer may be, for example, a linear phased array being mounted into the distal end of the catheter 222. A positioning system 224 attached to the catheter 222. The catheter 222 is intended to possibly represent multiple catheters inserted in the subject 144. The positioning system 224 is configured for rotating the catheter 222 about a longitudinal axis of the catheter 222. The positioning system 224 is shown as being connected to the hardware interface 154.

The computer system 152 shown in FIG. 1 is representative. Multiple processors and computer systems may be used to represent the functionality illustrated by this single computer system 152. The computer system 152 comprises the hardware interface 154 which allows the processor 156 to send and receive messages to components of the medical apparatus 100. The processor 156 is also connected to a user interface 158, computer storage 160, and computer memory 162.

Computer storage 160 is shown as containing a treatment plan 168. The treatment plan 168 contains instructions or a plan for treating the target volume 146. The treatment plan 168 may contain details of the subject anatomy 144 in relation to the target volume 146. It may describe the volumes to be destroyed and volumes to preserve around the target volume. The computer storage 160 is further shown as containing magnetic resonance thermometry and image data 170 that have been acquired by the magnetic resonance imaging module 106. The computer storage 160 is shown as further containing diagnostic images 172 that have been reconstructed from the magnetic resonance thermometry and image data. The computer storage 160 is shown as further containing coordinates 174 of the target volume 146. The computer storage 160 is shown as further containing heating control signals 178.

The computer memory 162 contains machine executable instructions 180, 182, 186, 188, 194 for operation by the processor 156. The computer memory 162 is shown as containing a medical apparatus control module 180. The medical apparatus control module 180 contains machine executable instructions which allow the processor 156 to control the overall functioning of the medical apparatus 100. The computer memory 162 is shown as further containing a catheter control module 182. The catheter control module 182 contains machine executable instructions which allow the processor 156 to control the functioning of the catheter 222.

The computer memory 162 is shown as further containing a magnetic resonance imaging control module 186. The magnetic resonance imaging control module contains machine executable code which allows the processor 156 to control the functioning and operation of the magnetic resonance imaging module 106. The computer memory 162 is shown as further containing an image reconstruction module 188. The image reconstruction module 188 contains machine executable code which is used by the processor 156 to reconstruct the magnetic resonance thermometry and image data 170 as images 172.

The computer memory 162 is shown as further containing heating control signal generation module 194. The heating control signal generation module 194 contains computer executable code which the processor 156 uses to generate the heating control signals 178. The heating control signals 178 may be generated in conjunction with the coordinates of the target volume 146, and the treatment plan 168.

In using such a medical apparatus 100, a clinician may insert the catheter 222 into the subject 144. The subject 144 is then placed such that the target volume 146 is within the imaging volume 138. The medical apparatus 100 is then operable to identify the location of the distal end and the target volume 146. As the focus of the catheter 222 is adjustable, the processor 156 is able to send commands to the positioning system 224 such that the target volume 146 is automatically heated by the catheter 222. The target volume 146 is controllably heated by the catheter 222 and is automatically controlled by the computer system 152.

Figure 2:
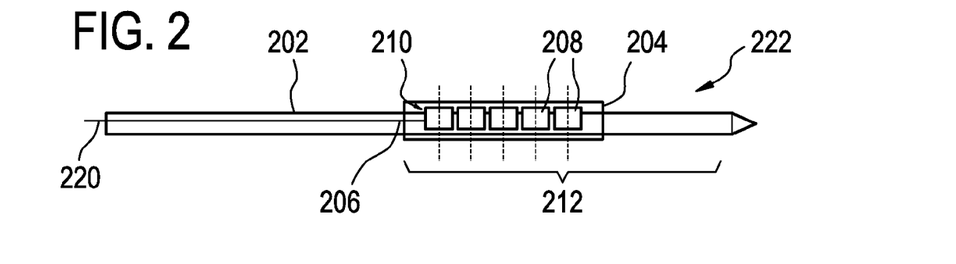
FIG. 2 shows a catheter.

FIG. 2 shows a top view of the catheter 222. The catheter 222 has a probe 202 with a distal end 212. At the distal end 212, there is an ultrasound transducer 204 having a flat surface 206 with an array 210 of transducer elements 208. The array 210 has its own individual electrical cable 220. When supplied with electrical power, the ultrasound transducer 204 deposits ultrasonic energy in the target volume 146 which is adjacent to or to the side of the probe 202.

Figure 3:
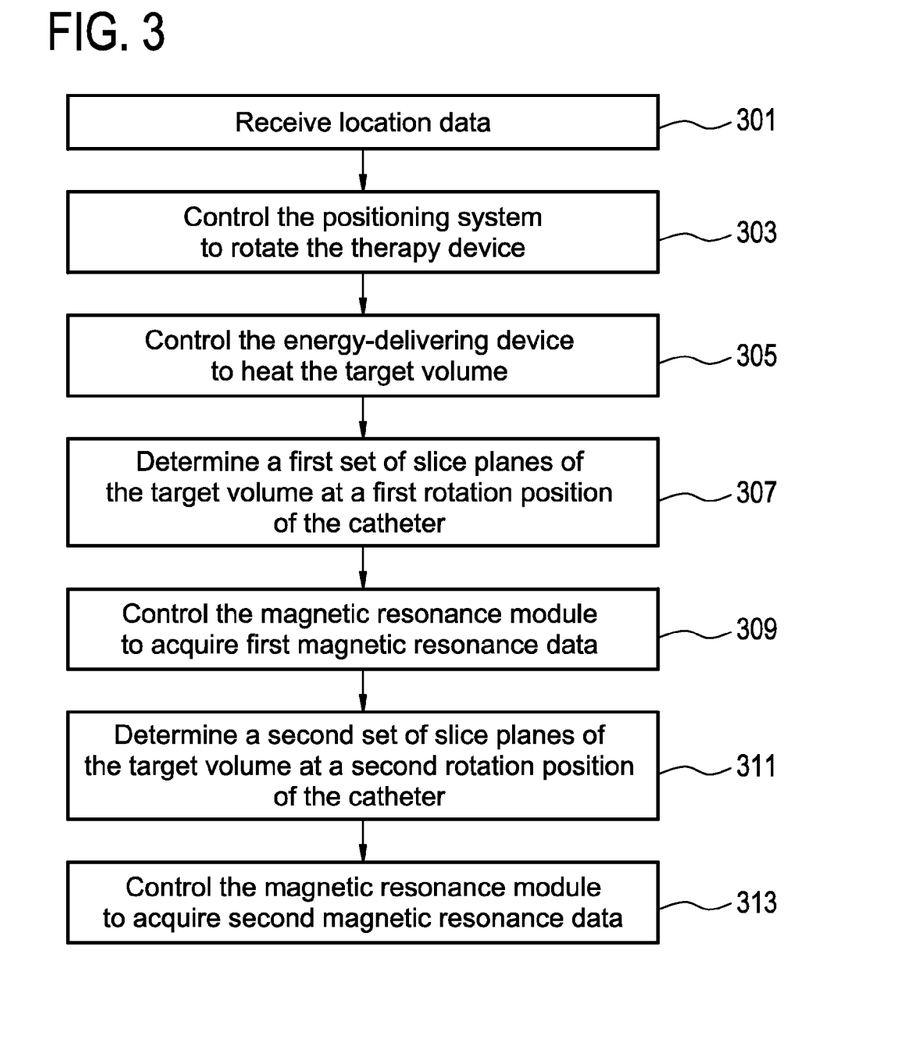
FIG. 3 is a flowchart of a method of controlling the medical apparatus.

FIG. 3 is a flowchart of a method for controlling a medical apparatus (e.g. 100). The medical apparatus comprises a therapy device such as the catheter 222. The therapy device comprises an energy delivering device such as the ultrasound transducer 204 for delivering energy to the target volume 146 within the imaging volume 138, the therapy device being operable to rotate about a longitudinal axis of the therapy device. The medical apparatus further comprises a magnetic resonance imaging module 106 and a positioning system 224.

In step 301 the processor 156 of the computer system 162 receives location data indicative (or descriptive) of the location of the target volume 146. The location of the target volume 146 may represent coordinates of the target volume 146 with respect to an MRI module reference frame.

In step 303, the processor 156 controls the positioning system 224 to rotate the therapy device about a longitudinal axis of the therapy device. The therapy device is rotated to expose different portions of the target volume 146.

In step 305, the processor 156 controls the energy-delivering device to deliver energy to the target volume 146 at a first rotation position relative to the longitudinal axis on a rotation trajectory of the therapy device using the location data. In case of the catheter, this may be done for example by supplying the transducer elements 208 with electrical excitations having adjustable phases in order to apply appropriate phase to each transducer element. In step 307, the processor 156 determines a first set of slice planes of the target volume 146 at the first rotation position to be imaged by the magnetic resonance imaging module 106. The first rotation position may be a non-rotating position. That is the first set of slice planes is a fixed set of slice planes. These first slice planes comprise transaxial planes perpendicular to the longitudinal axis.

In step 309, the processor 156 controls the magnetic resonance imaging module 106 to acquire first magnetic resonance data from the first set of slice planes. This is done by controlling the coil control devices to derive the gradient coil 134 to generate a respective first magnetic gradient field and to derive the radiofrequency coil 140 to generate a respective first radio-frequency field for each of the first set of slice planes in accordance with the first rotation position. The first magnetic resonance data may be for example first magnetic thermometry data.

Figure 5A:
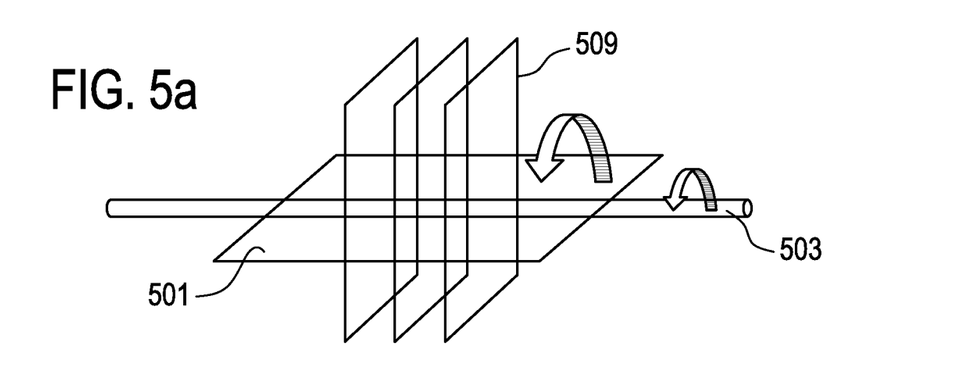
FIG. 5a illustrates a simplified schematic view of slice planes with one plane parallel to the longitudinal axis.
Figure 5B:
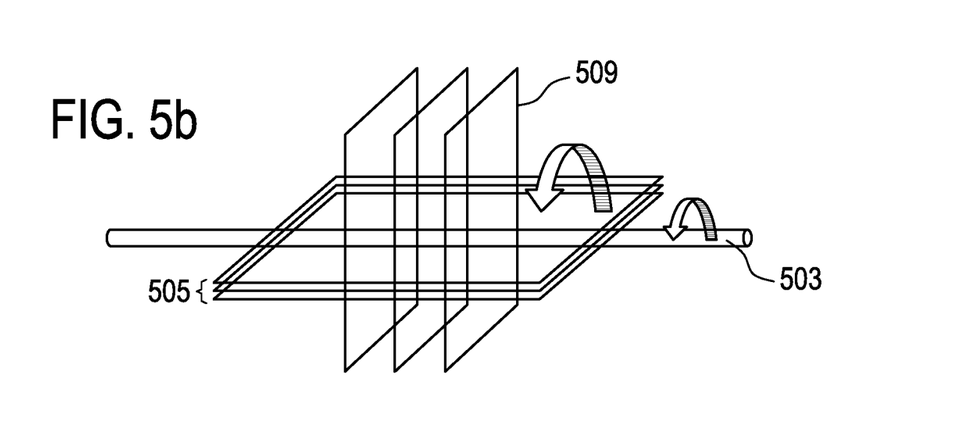
FIG. 5b illustrates a simplified schematic view with a plurality of parallel longitudinal planes.
Figure 5C:
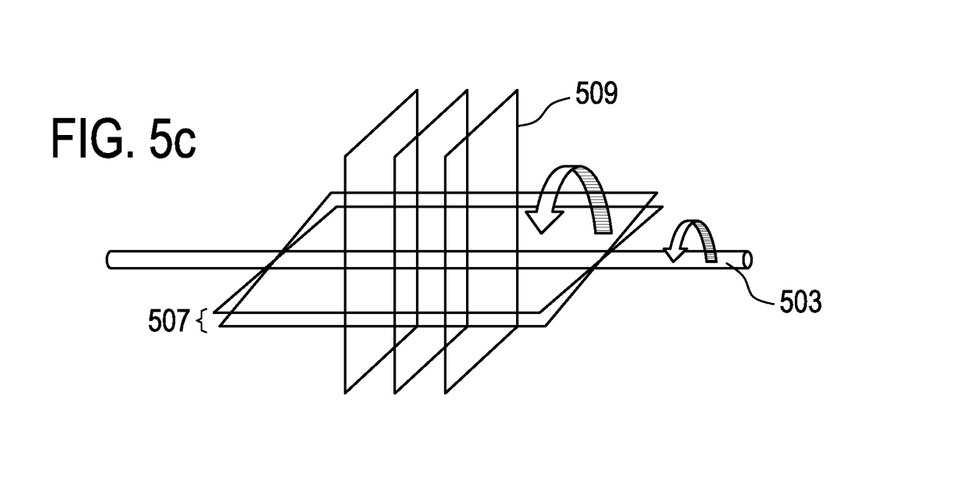
FIG. 5c illustrates a simplified schematic view with a plurality of longitudinal planes rotationally offset.

In step 311, the processor 156 determines a second set of slice planes of the target volume 146 at at least one second rotation position on the rotation trajectory to be imaged by the magnetic resonance imaging module 106. Each of the first and second set of slice planes comprises one slice plane 501 (FIG. 5.a) oriented in parallel to the longitudinal axis 503 (FIG. 5a). Each of the first and second set of slice plans further comprises one or more parallel slice planes 505 (FIG. 5.b) parallel to the longitudinal axis 503 (FIG. 5b). Each of the first and second set of slice plans further comprises one or more fan-shaped slice planes 507 (FIG. 5.c) parallel to the longitudinal axis 503 (FIG. 5c). The first set of slice planes further comprises planes 509 (FIG. 5c) being arranged along the longitudinal axis 503, and are perpendicular to the longitudinal axis 503.

In step 313, the processor 156 controls the magnetic resonance imaging module 106 to acquire second magnetic resonance data from the second set of slice planes. For that, the second rotation position is determined using the positioning system 224 and the coil control devices is controlled to derive the gradient coil 134 to generate a respective second magnetic gradient field and to derive the radiofrequency coil 140 to generate a respective second radiofrequency field for each of the second set of slice planes in accordance with the second rotation position. The first and second magnetic resonance data may be concurrently acquired. The second magnetic resonance data may be for example second magnetic thermometry data. The first (second) magnetic resonance thermometry data and first (second) magnetic resonance morphological data from the first (second) set of slice planes may be acquired with an interleaved pulse sequence.

Figure 4:
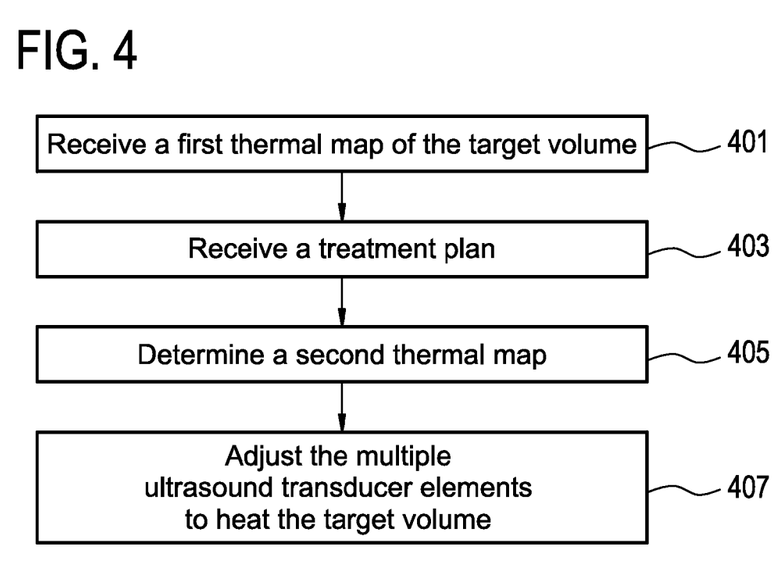
FIG. 4 is a flowchart of a method for adjusting the ultrasound transducer elements.

FIG. 4 shows a flowchart of a method for adjusting the ultrasound transducer elements 208. In step 401, the processor 156 receives a first thermal map of the target volume. The thermal map may be for example a spatial distribution assigned with colors representative of the temperature level in different areas of the target volume. In step 403, the processor 156 receives a treatment plan comprising instructions for controlling the operation of the ultrasound transducer 204 using the first thermal map together with the location data. The control may be performed for example by monitoring the heating in progress. In step 405, the processor 156 determines a second thermal map by using the first and second magnetic resonance thermometry data. The second thermal map may be obtained by adding the temperature increment measure at the second rotation position to the first thermal map. In step 407, the processor 156 controls the multiple ultrasound transducer elements 208 to adjust heating the target volume 146 in accordance with the first and second thermal maps. The control of the multiple ultrasound transducer elements 208 may be performed by supplying these transducer elements 208 with electrical excitations having adjustable phases in order to apply appropriate phase to each transducer element.

Figure 6:
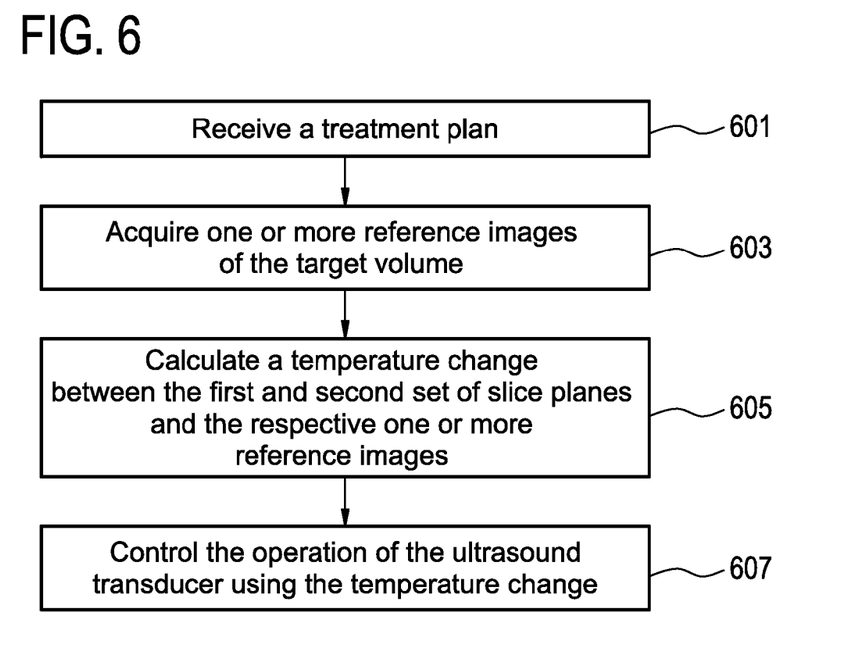
FIG. 6 is a flowchart of a method for heating the target volume using a phase-change based temperature imaging.

FIG. 6 shows a flowchart of a method for heating the target volume using a PRF based temperature imaging. In step 601, the processor 156 receives a treatment plan comprising instructions for controlling the operation of the ultrasound transducer 204. In step 603, the processor 156 acquires one or more reference images of the target volume 146 at predetermined positions relative to the longitudinal axis in a rotation trajectory of the catheter 222. In step 605, the processor calculates a temperature change between the first and second set of slice planes and the respective one or more reference images. In step 607, the processor 156 controls the operation of the ultrasound transducer to correct for the temperature change. The temperature change measurement provides the physician (clinician) with accurate temperature measurement and real-time thermometry data. Thus, the temperature may be optimized and adjusted continuously by using for example a proportional, integral and derivative (PID) controller. The PID controller may update the power level of the catheter taking into account the physical characteristics such as diffusion and absorption of the target volume. The PID controller may also adjust the rotation speed of the catheter.

LIST OF REFERENCE NUMERALS 100 medical apparatus
106 magnetic resonance imaging module
122 magnet
124 cryostat
126 superconducting coil
128 compensation coil
134 magnetic field gradient coil
136 magnetic field gradient coil power supply 138 imaging volume
140 radio frequency coil
144 subject
146 target volume
148 subject support
150 mechanical positioning system
152 computer system
154 hardware interface
156 processor
158 user interface
160 computer storage
162 computer memory
164 coil control devices
168 treatment plan
170 magnet resonance data
172 magnetic resonance image
174 coordinates of target volume
178 heating control signals
180 medical apparatus control module
182 catheter control module
186 magnetic resonance imaging control module
188 image reconstruction module
190 image registration module
192 actuator control signal generation module
194 heating control signal generation module
222 catheter
224 positioning system
202 probe
204 ultrasound transducer
206 flat surface
208 transducer element
210 array
212 distal end
301-309 steps
401-407 steps
501 one slice plane
503 longitudinal axis
505 parallel slice planes
507 fan-shaped slice planes
509 slice plane
601-607 steps

The invention claimed is:

1. A medical apparatus comprising:
a magnetic resonance imaging apparatus configured to acquire magnetic resonance data from nuclei of a subject located within an imaging volume;
a therapy device comprising an energy delivering device configured to deliver energy to a target volume within the imaging volume, the therapy device being operable to rotate about a longitudinal axis of the therapy device;
a positioning device for rotating the therapy device;
a memory configured to store machine executable instructions; and
a processor configured to control the medical apparatus, wherein execution of the machine executable instructions causes the processor to:
receive location data indicative of a location of the target volume;
control the positioning device to rotate the therapy device about the longitudinal axis;
acquire one or more reference images of the target volume at predetermined positions relative to the longitudinal axis in a rotation trajectory of the therapy device;
control the energy-delivering device to deliver energy to the target volume at a first rotation position relative to the longitudinal axis on the rotation trajectory of the therapy device using the location data;
determine a first fixed set of slice planes as transaxial planes perpendicular to the longitudinal axis at the first rotation position to be imaged by the magnetic resonance imaging apparatus, the first set of slice planes including a plurality of slice planes;
control the magnetic resonance imaging apparatus to acquire first magnetic resonance data from the first set of slice planes;
determine a second set of slice planes of the target volume as slice planes rotated relative to one another at at least one second rotation position around the rotation trajectory to be imaged by the magnetic resonance imaging apparatus, wherein the second set of slice planes comprises a plurality of parallel slice planes parallel to the longitudinal axis and each other and perpendicular to the first set of planes; and
control the magnetic resonance imaging apparatus to acquire second magnetic resonance data from the second set of slice planes;
wherein the first magnetic resonance data comprises first magnetic thermometry resonance data, and the second magnetic resonance data comprises second magnetic thermometry resonance data; and
wherein execution of the machine executable instructions causes the processor to calculate a temperature change between the first and second set of slice planes and the respective one or more reference images.

2. The medical apparatus of claim 1, wherein the therapy device comprises a catheter, wherein the energy-delivering device comprises an ultrasound transducer, wherein the ultrasound transducer is a linear phased array being mounted into a distal end of the catheter, wherein delivering energy to the target volume comprises heating the target volume.

3. The medical apparatus of claim 2, wherein execution of the machine executable instructions further causes the processor to acquire the second magnetic resonance thermometry data and second magnetic resonance morphological data from the second set of slice planes with an interleaved pulse sequence.

4. The medical apparatus of claim 2, wherein execution of the machine executable instructions further causes the processor to acquire the first magnetic resonance thermometry data and first magnetic resonance morphological data from the first set of slice planes with an interleaved pulse sequence.

5. The medical apparatus of claim 2, wherein execution of the machine executable instructions further causes the processor to:
receive a treatment plan comprising instructions for controlling the operation of the ultrasound transducer; and
control the operation of the ultrasound transducer to correct for the temperature change.

6. The medical apparatus of claim 2, wherein the ultrasound transducer comprises multiple ultrasound transducer elements, wherein execution of the machine executable instructions further causes the processor to:
receive a first thermal map of the target volume;
receive a treatment plan comprising instructions for controlling the operation of the ultrasound transducer using the first thermal map;
determine a second thermal map by using the first and second magnetic resonance thermometry data; and
control the multiple ultrasound transducer elements to adjust heating the target volume in accordance with the first and second thermal maps.

7. The medical apparatus of claim 1, further including a gradient coil, a radio-frequency coil and coil control devices, wherein the control of the magnetic resonance imaging apparatus to acquire second magnetic resonance data comprises:

controlling the coil control devices to cause the gradient coil to generate a respective first magnetic gradient field and to cause the radiofrequency coil to generate a respective first radio-frequency field for each of the second set of slice planes in accordance with the second rotation position.

8. The medical apparatus of claim 7, wherein the control of the magnetic resonance imaging apparatus to acquire first magnetic resonance data comprises:

controlling the coil control devices to cause the gradient coil to generate a respective second magnetic gradient field and to cause the radiofrequency coil to generate a respective second radio-frequency field for each of the first set of slice planes in accordance with the first rotation position.

9. The medical apparatus of claim 1, wherein execution of the machine executable instructions further causes the processor to concurrently acquire the first and second magnetic resonance data.

10. The medical apparatus of claim 1, wherein the first set of slice planes includes transverse planes arranged at intervals along the longitudinal axis.

11. A non-transitory computer readable medium containing machine executable instructions for execution by a processor controlling a medical apparatus, wherein the medical apparatus comprises a magnetic resonance imaging scanner for acquiring thermometric and morphological magnetic resonance data from nuclei of a subject located within an imaging volume; a therapy device comprising an energy-delivering device for delivering energy to a target volume within the imaging volume, the therapy device being operable to rotate about a longitudinal axis of the therapy device; a positioning apparatus for rotating the therapy device; wherein execution of the machine executable instructions causes the processor to:

receive location data indicative of the location of the target volume;

control the positioning apparatus to rotate the therapy device about the longitudinal axis;

control the energy-delivering device to deliver energy to the target volume at a first rotation position relative to the longitudinal axis on a rotation trajectory of the therapy device using the location data;

determine a first set of transaxial slice planes perpendicular to the longitudinal axis of the target volume at the first rotation position to be imaged by the magnetic resonance scanner, the first set including plurality of slice planes;

control the magnetic resonance imaging scanner to acquire thermometric and morphological magnetic resonance data from the first set of transaxial slice planes during the delivery of energy to the target volume;

determine a second set of longitudinal slice planes of the target volume at at least one second rotation position on the rotation trajectory to be imaged by the magnetic resonance imaging scanner during the delivery of energy to the target volume, the second set including a plurality of parallel slice planes parallel to the longitudinal axis and each other and perpendicular to the transaxial planes;

control the magnetic resonance imaging scanner to acquire thermometric and morphological magnetic resonance data from the second set of slice planes during the delivery of energy to the target volume wherein the thermometric and morphological magnetic resonance data is acquired concurrently from the first and second sets of slice planes and wherein the first set of slice planes are perpendicular to the second set of slice planes;

and calculate a temperature change map from the thermometric magnetic resonance data.

12. A method of controlling a medical apparatus, wherein the medical apparatus comprises a magnetic resonance imaging scanner configured to acquire magnetic resonance data from nuclei of a subject located within an imaging volume; a therapy device comprising an energy-delivering device configured to deliver energy to a target volume within the imaging volume, the therapy device being operable to rotate about a longitudinal axis of the therapy device; a positioning apparatus configured to rotate the therapy device; the method comprising:

receiving location data indicative of the location of the target volume;

controlling the positioning apparatus to rotate the therapy device about the longitudinal axis;

controlling the energy-delivering device to deliver thermal therapy to the target volume at a first rotation position relative to the longitudinal axis on a rotation trajectory of the therapy device using the location data;

determining a plurality of transaxial slice planes orthogonal to the longitudinal axis of the target volume at the first rotation position to be imaged by the magnetic resonance imaging scanner;

controlling the magnetic resonance imaging scanner to acquire thermometric and morphological magnetic resonance data from the plurality of transaxial slice planes during thermal therapy;

determining a plurality of longitudinal slice planes parallel to the longitudinal axis of the target volume at at least one second rotation position on the rotation trajectory to be imaged by the magnetic resonance imaging scanner, the longitudinal slice planes being parallel to each other and perpendicular to the transaxial slice planes;

controlling the magnetic resonance imaging scanner to acquire thermometric magnetic resonance data from the longitudinal set of slice planes during thermal therapy; and generating a temperature change map using at least the thermometric magnetic resonance data.

13. A medical apparatus comprising:

a catheter carrying a therapy device and configured for insertion into a patient and, for positioning the therapy device adjacent a target volume;

a therapy device being configured to deliver energy to the target volume, the therapy device being configured to rotate about a longitudinal axis of the therapy device;

one or more processors configured to:

receive location data indicative of a location of the target volume, control rotation of the therapy device about the longitudinal axis, control a magnetic resonance scanner to acquire one or more reference images of the target volume at predetermined positions along the longitudinal axis, control the therapy device to deliver thermal therapy to the target volume in each of parallel a plurality of longitudinal slice planes parallel to the longitudinal axis at each of a plurality of rotation positions using the location data, determine a plurality of transaxial slice planes perpendicular to the longitudinal axis, the plurality of transaxial slice planes being perpendicular to the plurality of longitudinal slice planes, control the magnetic resonance scanner to acquire at least thermometric resonance data from the plurality of parallel longitudinal slice planes and the plurality of transaxial slice planes during the delivery of the thermal therapy to the target volume at each of the plurality of rotation positions, and calculate a temperature change map indicative of temperature changes in the target volume from the acquired thermometric resonance data.

14. The medical apparatus of claim 13, wherein the one or more processors are further configured to:
control the magnetic resonance scanner to acquire both thermometric and morphological magnetic resonance data from the transaxial slice planes.

15. The medical apparatus of claim 14, wherein the one or more processors are further configured to:
control the magnetic resonance scanner to acquire both thermometric and morphological magnetic resonance data from the longitudinal slice planes.

16. The medical apparatus of claim 14, further including:
a display device configured to display an image of the temperature change map.

* * * * *